United States Patent [19]

Dingeldein et al.

[11] Patent Number: 4,869,906
[45] Date of Patent: Sep. 26, 1989

[54] TRICALCIUM PHOSPHATE FOR IMPLANT MATERIALS WHEREIN THE PORES OF THE TRICALCIUMPHOSPHATE ARE FILLED WITH ANTIBIOTIC AND AMINO ACID

[75] Inventors: Elvira Dingeldein, Dreieich; Helmut Wahlig, Darmstadt; Manfred Wotschokowsky, Darmstadt; Güter Moddelmog, Darmstadt, all of Fed. Rep. of Germany

[73] Assignee: Merck Patent Gesellschaft Mit Beschränkter Haftung, Fed. Rep. of Germany

[21] Appl. No.: 39,254

[22] Filed: Apr. 17, 1987

[30] Foreign Application Priority Data

Apr. 18, 1986 [DE] Fed. Rep. of Germany ....... 3613213

[51] Int. Cl.$^4$ .............................................. A61K 31/78

[52] U.S. Cl. ....................................... 424/423; 424/81
[58] Field of Search .................................. 424/81, 423

[56] References Cited

U.S. PATENT DOCUMENTS 4,373,217  2/1983  Draenert ............................ 523/116

OTHER PUBLICATIONS

Chem. Abstracts, vol. 97, entry 223006k.
Chem. Abstracts, vol. 93, entry 138032p.

Primary Examiner—Joseph L. Schofer
Assistant Examiner—Peter F. Kulkosky
Attorney, Agent, or Firm—Millen, White & Zelano

[57] ABSTRACT

A resorbable porous tricalcium phosphate, in which the pores are sealed with a filler mixture of an antibiotic and a filler, in particular an amino acid, is particularly advantageous for use in the preparation of bone cements.

12 Claims, No Drawings

TRICALCIUM PHOSPHATE FOR IMPLANT MATERIALS WHEREIN THE PORES OF THE TRICALCIUMPHOSPHATE ARE FILLED WITH ANTIBIOTIC AND AMINO ACID

BACKGROUND OF THE INVENTION

Cross Reference to Related Applications

This application is related to copending applications Ser. No. 853,320, filed Apr. 18, 1986, and Ser. No. 014,418, filed Feb. 12, 1987, which is a continuation of Ser. No. 711,504, filed Mar. 12, 1985, now abandoned.

This invention relates to an absorbable porous tricalcium phosphate, which is suitable as an additive for implant materials based on polyacrylates and/or polymethacrylates, wherein the pores are filled with an absorbable filler which is tolerated by the body.

It is known, for example, from German Offenlegungsschrift No. 2,905,878 (which corresponds to U.S. Pat. No. 4,373,217) that a tricalcium phosphate, which can be resorbed in the body, can be added to implant materials, in particular bone cements based on polyacrylates and/or polymethacrylates, in order to achieve good osseous fusion of the implant with the surrounding bone tissue. The problem that the pores of a porous tricalcium phosphate must be sealed by a suitable filler in order to avoid the pore system taking up liquid acrylate or methacrylate monomers and the disadvantages thereby caused during mixing of the cement has also already been discussed in German Offenlegungsschrift No. 2,905,878. The fillers mentioned therein for sealing the pores are glycerol, water or aqueous salt or buffer solutions, ethylene glycol, low molecular weight polyethylene glycols and lower alcohols, such as ethanol, n-propanol and isopropanol.

In addition to tricalcium phosphate, further additives are proposed or even in fact used for such implant materials, such as, for example, X-ray contrast agents, active compounds, such as, in particular, antibiotics, for controlling infections or fibers for improving the mechanical properties of the implant.

Although each of these additives by itself has a positive influence, there is nevertheless the risk that the mechanical stability and the mixing properties of the bone cement will be adversely influenced by the large number of additives.

SUMMARY OF THE INVENTION

An object of this invention is to provide bone cement containing additives wherein the previous problems with mechanical stability and mixing properties are reduced.

Upon further study of the specification and appended claims, further objects and advantages of this invention will become apparent to those skilled in the art.

According to this invention, it has now been found that a clear improvement can be achieved if a tricalcium phosphate in which the pores are sealed or filled with a mixture of an antibiotic and another filler is used as an additive.

This invention thus relates to a resorbable porous tricalcium phosphate which is suitable as an additive for implant materials based on polyacrylate and/or polymethacrylate, wherein its pores are filled with a resorbable filler tolerated by the body, characterized in that the filler is composed of at least two constituents, one constituent being an antibiotic.

This invention also relates to a process for the preparation of a resorbable porous tricalcium phosphate which is suitable as an additive for implant materials based on polyacrylates and/or polymethacrylates, wherein its pores are filled with a resorbable filler which is tolerated by the body, characterized in that the pores of the porous tricalcium phosphate are filled by bringing the tricalcium phosphate into contact with a solution of an antibiotic and another filler and then removing the solvent of the solution. Removal of the solvent is usually done by evaporation, e.g. under reduced pressure or by spraydrying.

The invention also relates to a precursor or kit for the preparation of a bone cement and the implant materials prepared therefrom, which are characterized in that they contain the tricalcium phosphate according to the invention.

The main advantage of the invention is that both the mixing properties of the bone cement and the mechanical properties of the hardened implant are substantially improved by the reduced number of additives. It has furthermore been found, surprisingly, that the release of the antibiotic or antibiotics from an implant according to the invention is significantly improved.

The term tricalcium phosphate used in the present application is to be understood as a generic term for a number of different materials which are essentially described by the chemical formula $Ca_3(PO_4)_2$, the calcium: phosphorus ratio approximately being 3:2. In addition to pure tricalcium phosphates, such as, for example, $\alpha$- or $\beta$-whitlockite, the term is also intended to include materials which can be described only approximately by the formula $Ca_3(PO_4)_2$, such as, for example, apatites or phosphorite. The tricalcium phosphate should in all cases be absorbable in the body.

These materials are known per se and can be prepared by known processes. These are essentially precipitation processes or sintering processes, or a combination of such processes. Precipitation or sintering processes for the preparation of the calcium phosphates are described in the standard works of inorganic chemistry, for example Gmelin, 8th Edition, Vol.28, Part B. By these methods tricalciumphosphate of any desired shape and size can be produced. Especially irregularly shaped or spherical particles of 2–300 $\mu$m diameter are preferred.

Starting materials which are used here are as a rule soluble calcium salts and soluble phosphates, or, for the sintering process, for example CaO, $Ca(OH)_2$, $CaCO_3$ and $CaHPO_4$, which are sintered together with $P_2O_5$ or with one another. By an appropriate choice of the sintering conditions the pore volume can e controlled in wide ranges, the pore volume becoming smaller with increasing temperature and duration of the sintering process, as described in U.S. Pat. No. 4,373,217.

Tricalcium phosphates obtained by precipitation processes are particularly preferably used in the present invention. These are as a rule relatively soft and have a large pore volume of the order of about 0.3–0.5 ml/g. The resorbtion of these materials obtained by precipitation is as a rule better than that of sintered materials.

According to the invention, the pores of these tricalcium phosphates are sealed with a mixture of an antibiotic and another filler. Aminoglycoside antibiotics, and in particular gentamicin, are preferably used as the antibiotics in the sealing mixture. Clindamycin and lincomycin and combinations of antibiotics, such as, for example, gentamicin with clindamycin, are furthermore also preferred.

Other fillers to be used in the sealing mixture are in principle all the physiologically tolerated substances which can be absorbed by the body and are immiscible with the acrylate monomers. Thus, for example, the alcohols already mentioned in German Offenlegungsschrift No. 2,905,878, such as, for example, glycerol, ethylene glycol and low molecular weight polyethylene glycols, or sugars, such as, for example, glucose or sucrose, sugar alcohols, such as, for example, mannitol or sorbitol, proteins and degradation products thereof, such as, for example, collagen, gelatine or elastin, and, in particular, also amino acids, such as, for example, valine, histidine, leucine, isoleucine, threonine, arginine, lysine and alanine, can be used. Threonine and arginine are particularly preferably used.

Although the pore volume of a selected tricalcium phosphate is fixed, the amount of fillers can be varied within relatively wide limits without the hollow space system of the tricalcium phosphate taking up monomers during mixing of the bone cement. This shows that evidently the entire pore volume of the tricalcium phosphate does not have to be filled with the fillers. Instead, all that is evidently sufficient is enough filler to seal the pores externally.

Thus, if a precipitated tricalcium phosphate which has a relatively high pore volume is used, about 2-20, in particular about 5-15% by weight of antibiotic and about 0.5-5, in particular about 0.8-3.2% by weight of the other filler are employed, based on the total weight of the filled tricalcium phosphate. Only if a liquid filler, such as, for example, glycerol, is used as the other filler higher amounts of up to about 30% by weight thereof can be employed. The same relative proportions of antibiotic and filler are used in the case of a sintered material, bearing in mind, however, that due to the reduced pore volume the absolute content of antibiotic and filler is preferably in the lower part of the above range.

These fillers are applied to the tricalcium phosphate by methods which are known per se. Thus, for example, the tricalcium phosphate can be impregnated with a solution of the fillers and the solvent can then be evaporated. In order to achieve intensive penetration of the solution into the pore system of the tricalcium phosphate, it is possible, for example, either to carry out this operation under increased pressure or to evacuate the tricalcium phosphate powder before the addition of the filler solution. Possible solvents for the fillers are both organic solvents and, in particular, water or aqueous buffer solutions with a physiological pH.

A particularly advantageous product is obtained by spray-drying. Since the tricalcium phosphate preferably employed has a very small particle size in the range of about 2-300 μm, in particular about 20-200 μm, suspensions of the tricalcium phosphate in a solution of the fillers can be spray-dried by customary methods. The conditions to be applied here, such as concentrations of the suspension, temperature and pressure, are familiar to the expert and can, if necessary, be optimized with respect to the particular components used by a few preliminary experiments in accordance with methods described in textbooks, such as, for example, in Sucker, Fuchs and Speiser "Pharmazeutische Technologie" ("Pharmaceutical Technology"), Gerog-Thieme-Verlag, Stuttgart, 1978.

The tricalcium phosphate particles obtained as a free-flowing powder by one of these methods can be used directly or after sterilization, for example by irradiation or gassing with ethylene oxide, in the preparation of bone cements. The known bone cements are prepared by mixing about two parts by weight of a fine-particled prepolymer, in particular polymethyl methacrylate or a copolymer of methyl acrylate and methyl methacrylate, containing a polymerization catalyst (for example dibenzoyl peroxide) with about one part by weight of the liquid monomer, for example, acrylic acid or methyl methacrylate or mixtures thereof, containing an accelerator (for example dimethyl-p-toluidine) to give a mass which can be shaped and which is implanted in the body and hardens there. Such bone cements are commercially available, for example, under the tradename Palacos ®.

Bone cements with the tricalcium phosphate according to the invention are prepared in an analogous manner by either mixing the three constituents of prepolymer, tricalcium phosphate and monomer or first admixing one of the other two constituents to the tricalcium phosphate.

Implantation materials according to the invention can thus, for example, comprise a polymer of polyacrylates, polymethacrylates, or mixtures thereof, a liquid monomer of acrylic and/or methacrylic acid ester and 3-20 wt. % of resorbable tricalcium phosphate material prepared in accordance with the invention.

The commercially available form of the bone cement will preferably be such that the solid and liquid constituents are indeed separate but are in a kit or ready-to-use packs in amounts matched to one another. A ratio of about 40 g of solid (i.e., prepolymer and tricalcium phosphate) to about 20 ml of liquid monomer is preferably maintained here.

Other ratios of about 10-30 ml of liquid monomer to 40 g of solid are, in principle, also possible. The proportion of tricalcium phosphate according to the invention within the solid component is as a rule about 5-30, in particular about 8-20% by weight.

In addition to the tricalcium phosphate according to the invention, other additives can be admixed to the solid component. Thus, for example, another tricalcium phosphate content without fillers, such as, for example, an essentially pore-free sintered apatite, or an X-ray contract agent, such as, for example, zirconium dioxide, can be admixed in amounts of 0-20% by weight. The latter constituent can be dispensed with, however, if the tricalcium phosphate components already effect sufficient X-ray contrast.

To improve the mechanical properties of the implant, it is also possible to add fiber constituents, such as, for example, carbon fibers, glass fibers, or fibers of plastic, such as, for example, those of polymethyl methacrylate or Aramite, in amounts of about 0-30% by weight.

The solid component can additionally also contain other materials, such as, in particular, bioactive glass ceramics, in amounts of 0-50% by weight. However the solid component is in all cases chosen so that the ratio of about 40 g of solid to about 20 ml of monomer is essentially observed, that is to say as the content of other additives increases the content of the prepolymer decreases.

It has already been mentioned that compared with an implant material to which a pulverulent antibiotic has been added, the release of the antibiotic from an implant material according to the invention is significantly improved. In fact, release is found to be improved by a factor of 5–10. A very useful and advantageous new tricalcium phosphate component is thus available for the preparation of bone cements.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

97.6 g of tricalcium phosphate (E. Merck, Darmstadt, Cat. No. 2194) with a particle size of less than 63 m are suspended in a solution, brought to pH 7.4, of 0.8 g of L-arginine and 1.6 g of gentamicin sulfate. The suspension is sprayed in a spray-drying unit (nozzle pressure: 2 bar; air flow 380 m$^3$/hour; intake temperature: 200° C.; discharge temperature: 65° C.).

EXAMPLE 2

The procedure followed is analogous to Example 1, but 1.6 g of L-arginine, 1.6 g gentamicin sulfate and 96.8 g of tricalcium phosphate are employed.

EXAMPLE 3

The procedure followed is analogous to Example 1, but 1.6 g of L-arginine, 4.0 g of gentamicin and 94.4 g of tricalcium phosphate are employed.

EXAMPLE 4

The procedure followed is analogous to Example 1, but 1.6 g of L-arginine, 8.0 g of gentamicin and 90.4 g of tricalcium phosphate are employed.

EXAMPLE 5

The procedure followed is analogous to Example 1, but 1.6 g of L-arginine, 16.0 g of gentamicin and 82.4 g of tricalcium phosphate are employed.

EXAMPLE 6

The procedure followed is analogous to Example 1, but 5.0 g of L-arginine, 8.0 g of gentamicin and 87 g of tricalcium phosphate are employed.

EXAMPLES 7–12

The procedure followed is analogous to Examples 1–6, but L-threonine is employed instead of L-arginine.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a resorbable porous tricalcium phosphate suitable for use as an additive in implant materials comprising polyacrylates, polymethacrylates or mixtures thereof, pores of said tricalcium phosphate material being sealed with a physiologically tolerable absorbable filler, the improvement wherein said filler further comprises an antibiotic.

2. A tricalcium phosphate material according to claim 1, wherein said amino acid is threonine or arginine.

3. A tricalcium phosphate material according to claim 1, wherein said antibiotic is gentamicin, clindamycin, lincomycin, or mixtures thereof.

4. A tricalcium phosphate material according to claim 1, wherein the amount of said antibiotic is about 2–20% by weight based on the weight of the tricalcium phosphate.

5. A tricalcium phosphate material according to claim 1, wherein the amount of said filler exclusive of the antibiotic is about 0.5–5% by weight.

6. A tricalcium phosphate according to claim 1, in the form of particles having a particle size of about 2–300 μm.

7. In a process for preparing resorbable porous tricalcium phosphate suitable for use as an additive for implant materials comprising polyacrylates, polymethacrylates, or mixtures thereof, the improvement comprising sealing the pores of said tricalcium phosphate material with a resorbable physiologically tolerable filler by contacting said tricalcium phosphate material with a solution comprising an aminoglycoside antibiotic, an amino acid, and solvent.

8. A process according to claim 7, wherein tricalcium phosphate material is suspended in said solution and further comprising spray drying the resultant suspension.

9. A kit for the preparation of a bone cement comprising a first package containing a prepolymer in particle form and a resorbable tricalcium phosphate material according to claim 1, and a second package containing a liquid monomer, said prepolymer and liquid monomer capable of forming a polyacrylate, a polymethyl acrylate, or mixtures thereof, and said first package containing about 5–30% by weight of said tricalcium phosphate material.

10. A kit according to claim 9, wherein said first package contains about 8–20% by weight of said tricalcium phosphate material.

11. A kit according to claim 9, wherein the contents of said first and second package are in a ratio of about 40 g of solid in said first package to about 20 ml of monomer in said second package.

12. An implantation material comprising a polymer of polyacrylates, polymethacrylates, or mixtures thereof a liquid monomer of acrylic and/or methacrylic acid ester and 3–20% by weight of a resorbable tricalcium phosphate material according to claim 1.

* * * * *

UNITED STATES PATENT AND TRADEMARK OFFICE
CERTIFICATE OF CORRECTION

PATENT NO. : 4,869,906

DATED : September 26, 1989

INVENTOR(S) : ELVIRA DINGELDEIN ET AL

It is certified that error appears in the above-identified patent and that said Letters Patent is hereby corrected as shown below:

Column 6, claim 1, line 9:

reads "filler, the improvement wherein said filler further com-"

should read --filler, the improvement wherein said filler com- --

Column 6, claim 1, line 10:

reads "prises an antibiotic."

should read -- prises an amino acid and an aminoglycoside antibiotic. --

Signed and Sealed this

Fourth Day of September, 1990

Attest:

HARRY F. MANBECK, JR.

*Attesting Officer*      *Commissioner of Patents and Trademarks*